United States Patent [19]
Rosenberg

[11] Patent Number: 6,106,781
[45] Date of Patent: *Aug. 22, 2000

[54] CONVEYING SYSTEM FOR ANALYTICAL SAMPLES

[75] Inventor: Burkard Rosenberg, Horw, Switzerland

[73] Assignee: Roche Diagnostic Corporation, Indianapolis, Ind.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/962,218

[22] Filed: Oct. 31, 1997

Related U.S. Application Data

[63] Continuation of application No. 08/698,415, Aug. 15, 1996, abandoned, which is a continuation of application No. 08/521,257, Aug. 30, 1995, abandoned, which is a continuation of application No. 08/188,341, Jan. 27, 1994, abandoned, which is a continuation of application No. 08/036,118, Mar. 23, 1993, abandoned.

[30] Foreign Application Priority Data

Apr. 6, 1992 [EP] European Pat. Off. ............. 92105901

[51] Int. Cl.[7] .................................................. G01N 35/02
[52] U.S. Cl. .................................. 422/64; 422/63; 422/65; 436/43; 436/48
[58] Field of Search ................................ 422/63–67, 103, 422/104; 436/43, 47–49, 54

[56] References Cited

U.S. PATENT DOCUMENTS

| | | |
|---|---|---|
| 3,115,966 | 12/1963 | Leiter . |
| 3,322,958 | 5/1967 | Heiss . |
| 3,432,049 | 3/1969 | Howells et al. . |
| 4,518,264 | 5/1985 | Nohso ..................................... 366/208 |
| 4,699,766 | 10/1987 | Yamashita . |
| 4,755,055 | 7/1988 | Johnson et al. . |
| 4,844,868 | 7/1989 | Rokugawa . |
| 4,861,553 | 8/1989 | Manwhirt et al. . |
| 5,066,135 | 11/1991 | Meyer et al. . |

FOREIGN PATENT DOCUMENTS 0 099 103  1/1984  European Pat. Off. .

*Primary Examiner*—Long V. Le
*Attorney, Agent, or Firm*—Gibbons, Del Deo, Dolan, Griffinger & Vecchione

[57] ABSTRACT

A processing station is provided for removing a cuvette 1 from a transport magazine 2, for transferring the cuvette to a position for processing in order to carry out a processing step such as adding samples, adding reagents or mixing, and for returning the cuvette to the transport magazine after processing.

3 Claims, 3 Drawing Sheets

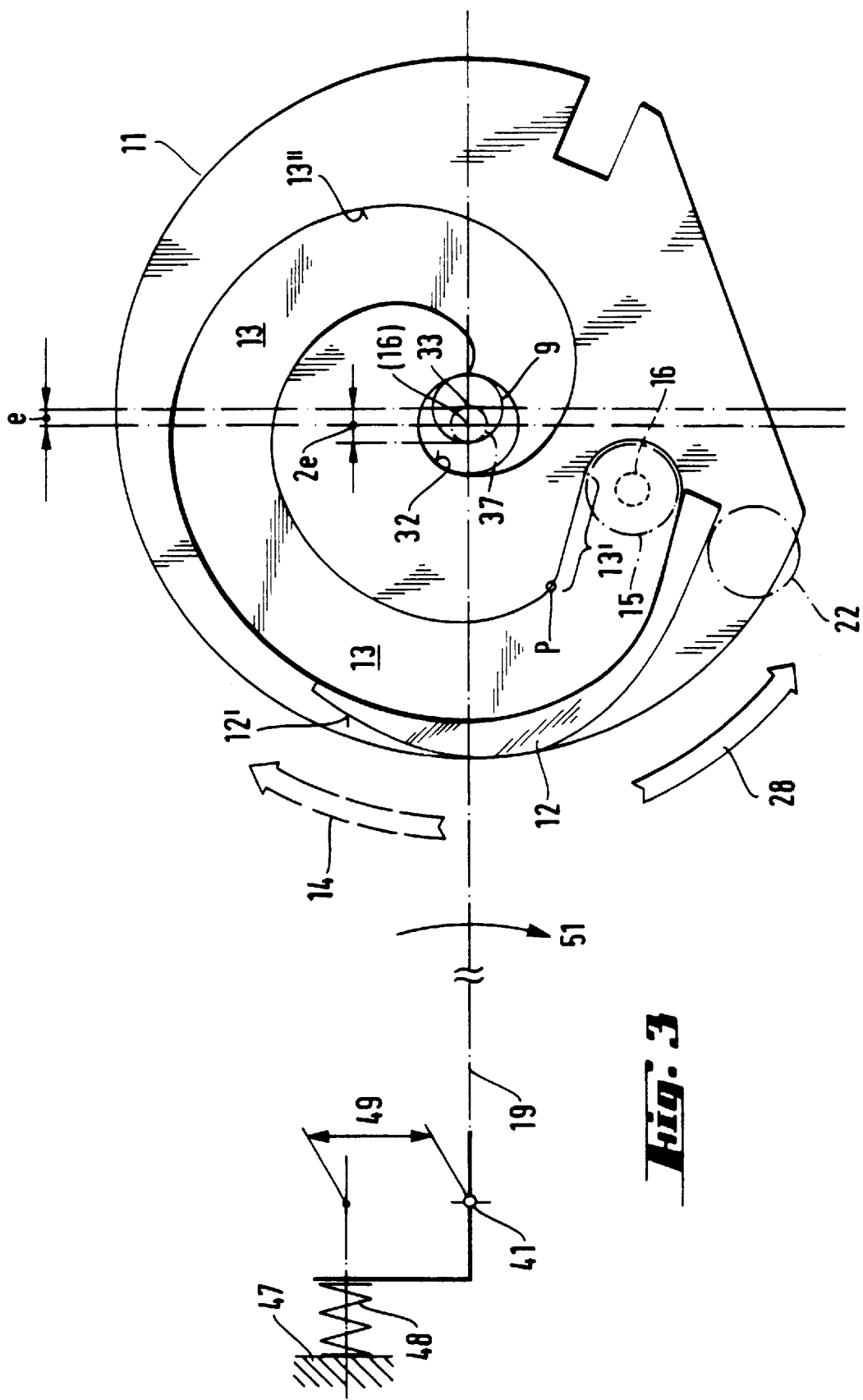

CONVEYING SYSTEM FOR ANALYTICAL SAMPLES

CROSS REFERENCE TO RELATED APPLICATIONS

The instant Application is a continuation of U.S. application Ser. No. 08/698,415 filed Aug. 15, 1996 now abandoned which is a continuation of U.S. application Ser. No. 08/521,257 filed Aug. 30, 1995, now abandoned, which is a continuation of U.S. application Ser. No. 08/188,341 filed on Jan. 27, 1994, now abandoned, which is a continuation of U.S. application Ser. No. 08/036,118, filed Mar. 23, 1993, now abandoned.

BACKGROUND OF THE INVENTION

The invention relates to a station for processing analytical samples in cuvettes in a device for chemical and biochemical analysis comprising a conveyor for conveying cuvettes to individual processing stations.

Automatic analytical devices usually operate on the following principle: samples for analysis or parts thereof are placed in cuvettes and then subjected to a number of processing steps such as addition (pipetting) of reagents, mixing, incubation etc., and the reactions are measured repeatedly during processing and/or once at the end of processing. The operating sequence is usually as follows: the cuvettes containing the samples for analysis are disposed in a fixed sequence on a conveying means and travel through various processing stations, or alternatively in "batch" processing, as conventional in the case of "centrifugal" analysers devices, all the cuvettes are disposed on a carrier (rotor) and are subjected substantially simultaneously to be the processing steps and measurements. Analytical systems operating on these principles give good service in large clinics and analytical centres where large numbers of samples have to processed.

In view, however, of the present variety of possible forms of analysis and the medical requirements, particularly in clinical chemistry, it has been found that the automatic analytical devices hitherto used conventionally for throughput of large quantities of samples are not sufficiently flexible for providing analytical profiles (full random access) specifically adapted to individual patients or medical conditions, while still being able to handle a large number of samples from patients.

SUMMARY OF THE INVENTION

The aim of the invention, in general, therefore is to provide an analytical system which takes account of these requirements by being able to process a large number of samples for analysis with great flexibility with regard to the analytical profile applied to the individual sample. More particularly, the aim is to provide a processing station for an aforementioned analytical system.

This is achieved according to the invention by providing means for removing individual cuvettes from the conveyor, for transferring the individually to the position for processing and for returning the cuvettes to the conveyor after processing.

Preferably the aforementioned means comprise a change-over and positioning device and a device for simultaneously controlling the positions of the change-over and positioning device and controlling a mixing process during processing.

The processing station according to the invention is of use in an analytical device which is described in the simultaneously-filed European patent application No. 92.105903. Reference is hereby made to this description.

An embodiment of the invention will now be described with reference to the accompanying drawings, in which:

DESCRIPTION OF THE FIGURES

FIG. 3 is a diagrammatic view of the control cam arrangement.

DETAILED DESCRIPTION OF THE INVENTION AND PREFERRED EMBODIMENTS

Figure 1:
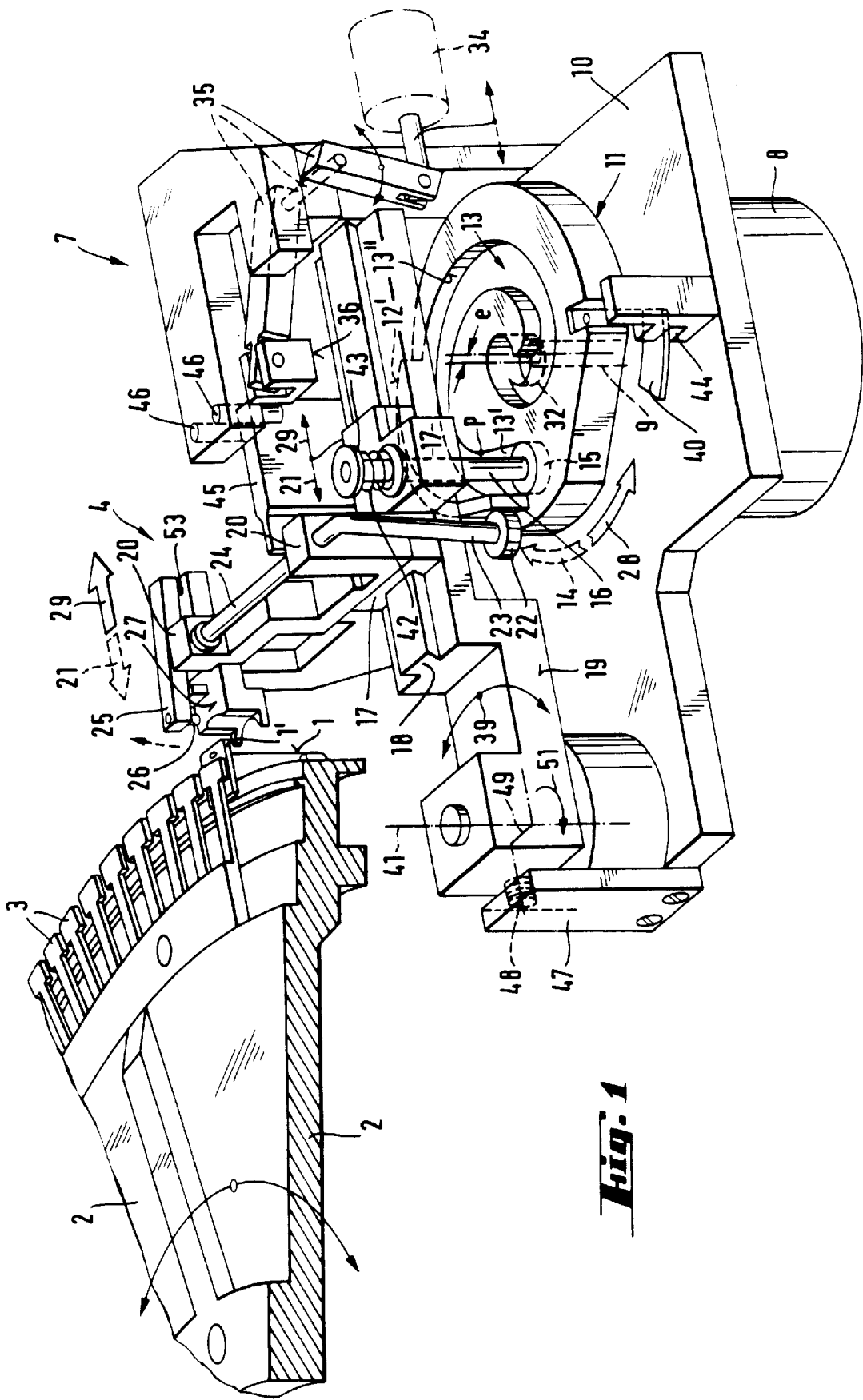
FIG. 1 is an axonometric representation of the device before removal of a measuring cuvette from a rotor magazine.
Figure 2:
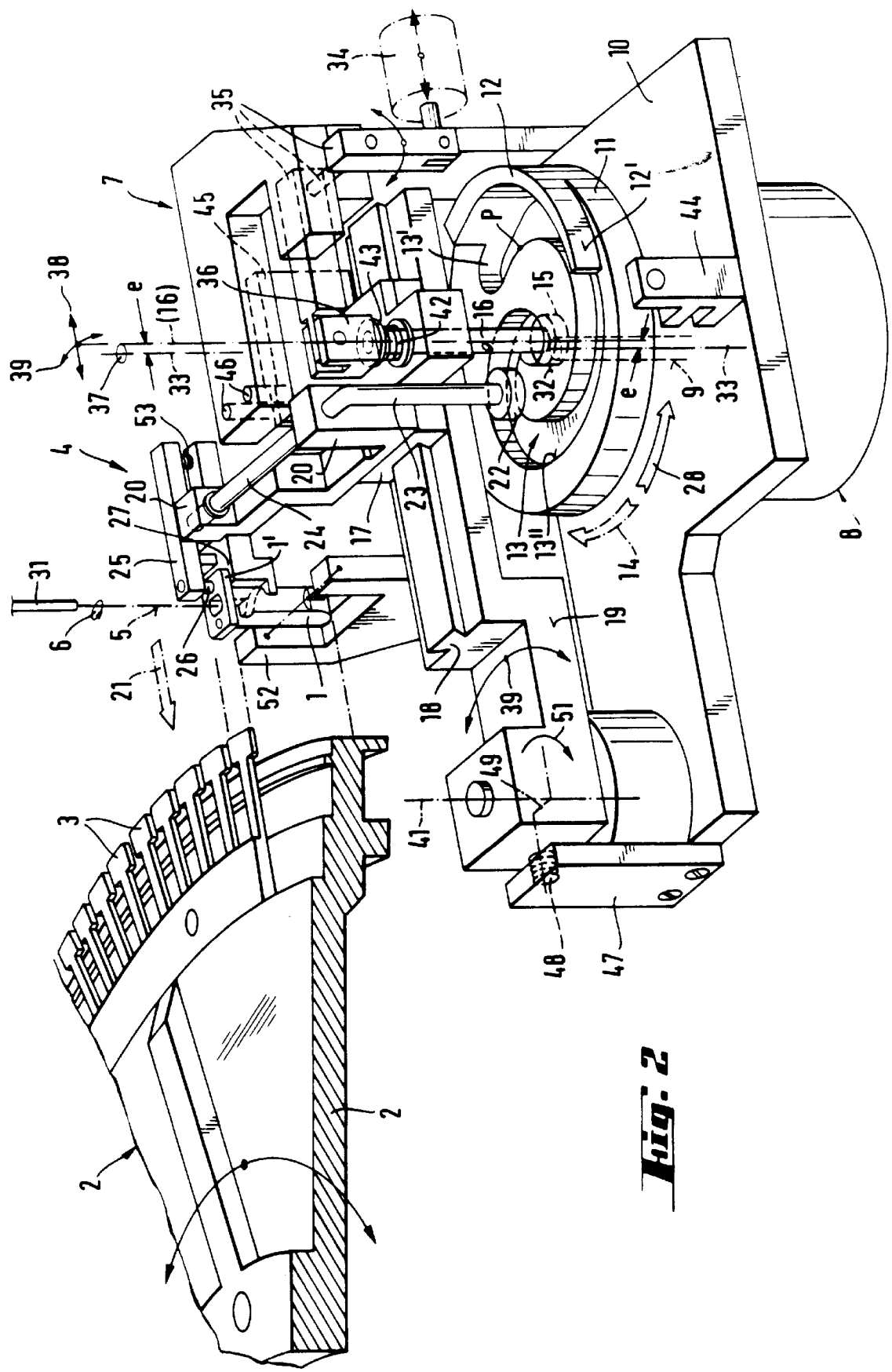
FIG. 2 is a view corresponding to FIG. 1 in the pipetting position of the cuvette and mixing of the cuvette contents.

A circular rotor 2 shown in FIGS. 1 and 2 and rotatable by a drive (not shown) through exact angular steps in both directions of rotation, serves as a transport magazine for cuvettes 1. The cuvettes 1 are held at the outer edge of the rotor, in that they have a flange 1' on their top surface which rests on a flat annular surface at right angles to the rotor axis, and simultaneously one wall surface of each cuvette abuts the substantially cylindrical outer surface of the rotor, and also resilient tongues 3 are associated with each cuvette position and extend radially over the cuvette and to this end, on their underside, have a projection (not shown) which engages in a recess in the cuvette flange 1'. The resilient holder holds the cuvettes so that they cannot fall out even when the rotor rotates. On the other hand, by means of the resilient holder, the cuvettes can easily be removed or inserted manually or by a mechanical gripping mechanism.

A detailed description of the rotor and the operation thereof is given in the simultaneously filed European patent application No. 92.105902. Reference is hereby made to this description.

A processing station W is disposed in an exactly defined position relative to the rotor 2. In the present embodiment, the processing station is for adding reagents to the samples in the cuvettes and mixing the reagents with the samples. The processing station substantially comprises a mixing device 7 and a change-over and positioning device 4 for transferring the cuvettes from the rotor to a pipetting and mixing position and back to the rotor.

Other processing stations arranged and equipped according to the same principle are used e.g. for introducing samples into the cuvettes, for certain measurements, for incubation etc.

The mixing device 7 moves the cuvette along a mixing curve 6, after the device 4 has brought the cuvette into the pipetting and mixing position. To this end, the device 4 is constructed so that the parts thereof holding the cuvette are driven in substantially elliptical motion corresponding to the mixing curve 6. This will be explained in detail in the following description.

A servomotor 8, which controls all operating sequences, is disposed below a stationary baseplate 10. The servomotor 8 has a shaft 9 extending through the baseplate 10 and bearing a control disc 11 which comprises a cam 12 and a groove 13. The control groove 13 has a substantially spiral shape and extends over an angle of about 360° from the centre of the control disc to near the periphery thereof. A cam roller 15 is disposed in the control groove and is rotatably mounted on a push rod 16. The push rod 16 is non-rotatably connected to a slide 17 which slides along a straight line on a guide 18 in a substantially radial direction towards the rotor 2. The guide 18 is part of a swivel arm 19. The direction of motion of the slide 17 is shown by an arrow 21 for motion towards the rotor and 29 for motion away from the rotor.

Another cam roller 22 is rotatably mounted on a crank arm 23 and positioned so that during a certain angular rotation of the control disc 11, the roller 22 is guided along the outer surface of the cam 12. The crank arm 23 is integral with a shaft 24 which is mounted for rotation in two struts 20 which extend vertically from the slide 17. At its other end, the shaft 24 bears a lever-like gripper 25. When the cam roller 22 and the crank arm 23 are moved outwards by the cam 12, the shaft 24 rotates and raises or lowers the gripper 25.

On its underside, the gripper 25 bears a cam 26 which is dimensioned so that it can engage in the recess in the flange on the cuvette.

A spiral spring 53 is clamped against an abutment under the other end of the gripper and ensures that the gripper is always in a "closed" inoperative position when not actively opened.

An anvil 27 is disposed below the gripper 25 and, on its side facing the rotor 2 and cuvettes 1, has an end face profiled to correspond to the shape of the cuvette, the top surface of the end face being exactly level with the annular surface on which the cuvette flange bears on the rotor. The anvil 27 co-operates with the gripper 25. These two parts hold a cuvette, so as to remove it from the rotor and transfer it to the pipetting and mixing position 5. In position 5, the cuvette is at the place where a pipetting syringe 31 (FIG. 2) is lowered into the ejection position inside the cuvette.

In addition to the previously mentioned spiral groove 13, the control disc has a central bore 32 which is deeper than the spiral groove and is disposed at the inner end thereof, eccentrically relative to the shaft 9.

An electromagnet 34 disposed on the slide moves a hammer 36, via a linkage 35, into a top and a bottom position. In the bottom position the hammer 36 presses the push rod 16 and consequently the cam roller 15 into the central recess in the control groove, against the pressure of a helical spring 42 disposed between the bearing and the head 43 of the push rod 16. In its top position, the hammer 36 release the head 43 of the push rod 16.

A rotation pick-up 44 is disposed on the periphery of the control disc 11 and responds to as part of the disc, e.g. to a vane 40 disposed on it and used for resetting the control disc 11.

The swivel arm 19 is mounted for rotation around a shaft 41 permanently connected to the baseplate 10. A helical spring 48 is disposed between the arm 19 and a bracket 47 and is laterally offset from the shaft 41. As a result of the lateral offset, the spring exerts a torque on the arm 19, thus forcing it into a defined inoperative position. The inoperative position is defined so that in it, the change-over and positioning device moves exactly radially towards the rotor. It also helps to introduce the cam roller 15 into the control cam 13 after it has been raised from the bore 32 during the change in direction of rotation from anti-clockwise 28 to clockwise 14.

The slide 17 has an additional guide in the form of a vertical guide plate 45 and two guide pins 46.

A light barrier is disposed in a fixed position relative to slide 17 and arm 19 and detects the presence or absence of a cuvette. If no cuvette has been gripped, the fault is reported to the system, after which appropriate action is taken.

The purpose and co-operation of the aforementioned components is as follows:

While the rotor 2 is stationary, the change-over and positioning device 4 takes a cuvette 1 from the rotor 2 (FIG. 1) and transfers it to a pipetting position 5 (FIG. 2).

The needles 31 are then used for pipetting and simultaneous mixing by closed shaking movements in the form of a mixing curve 6 generated by the mixing device 7 as described hereinafter. During the mixing operation, the pipetting needle remains inserted in the cuvette and delivers the reagents to be pipetted. Mixing is particularly efficient if simultaneous with pipetting.

Next, the cuvette 1 filled with the mixture is returned by the device 4 to the rotor magazine 2, which conveys the cuvette 1 to other working stations.

The device 4 and the mixer 7 are driven by a common motor 8. The cuvettes 1 are taken from rotor 2 as follows:

The motor 8, via the shaft 9, drives the control disc 11 comprising the cam 12 and the spiral groove 13.

When the control disc 11 rotates anticlockwise 28, the roller 15, push rod 16, slide 17 and device 4 are moved on the guide 18 of the swivel arm 19 in the direction 21 towards the rotor 2 (FIG. 1) via a straight, radially outwardly acting portion 13' of the control groove 13.

At the same time, the cam 12 acts on roller 22 via the crank arm 23 and shaft 24 so as to open the gripper 25 of the change-over and positioning device 4. After device 4 reaches its foremost position, the cam part 12' closes the gripper 25 under the action of spring 53. The cam 26 and anvil 27 grip the flange 1' of the cuvette 1.

Next (point P on the control cam 13, 13'), the push rod 16, cam roller 15 and spiral groove 13 move the slide 17 and device 4 from the rotor magazine 2 in the direction 29 and thus transfer the cuvette 1 from the range of operation of rotor 2 to the pipetting and mixing position 5 (FIG. 2).

In position 5, one or more pipettes 31 can be used for pipetting with simultaneous or subsequent mixing by shaking. The mixer drive operates as follows:

In the pipetting and mixing position 5 in FIG. 2, the cam roller 15 is at the inner end of the control groove 13 and initially is exactly above the bore 32, which is eccentric (e) relative to the centre 33 of the shaft 9. The electromagnet 34, the linkage 35, the hammer 36 and the push rod 16 insert the cam roller 15 into the eccentric bore 32 below the level of the control cam 13. The bore 32, which is disposed in the control disc 11 and is eccentric (e) relative to the shaft 9, additionally rotates in the direction 28, resulting in a circular, eccentric drive 37 of the cam roller 32 and push rod 16 around a diameter 2e (FIG. 3), thus generating two superposed shaking and mixing sequences, i.e. a linear oscillating mixing motion in a direction 38 along the guide 18, and an oscillating pivoting motion 39 around the shaft 41 of the swivel arm 19. The two motion sequences 38 and 39 overlap at the pipetting and mixing position 5 to form an elliptical mixing curve 6.

During mixing, the cam roller 22 is outside the range of action of the control cam 12, and is thus positioned above the disc 11 in a radially inner position relative to the cam (FIG. 2).

The spring 42 biases the push rod 16 so that during mixing the push rod always remains vertical with its head 43 against the hammer 36, but can move freely horizontally under the hammer in the directions 38 and 39 (FIG. 2).

After pipetting and mixing, the filled cuvette 1 is returned to the rotor 2 as follows (FIG. 1):

The electromagnet 34 after actuation, the linkage 35 and the spring 42 raise the hammer 36, so that the push rod 16 and roller 15 are raised vertically out of bore 32 to the level of the control cam 13. The direction of rotation changes to clockwise 14. The cam roller 15 engages the control groove 13 and, via the push rod 16, guides the slide 17 and the change-over and pipetting device 4 along the guide 18 in the direction 21 towards the rotor 2.

In the process the cuvette 1 is delivered to the rotor 2, and meanwhile the cam roller 22 has run up to the cam part 12' and opens the gripper 25 via the crank 23 and shaft 24.

By means of the straight curve portion 13', the change-over and positioning device 4 is then moved a distance from the rotor 2 and consequently out of its range of action.

The rotor then moves to the next position, e.g. to transfer the cuvette to another station and bring a new cuvette 1 to the pipetting and mixing position. The sequence of operations recommences as described.

What is claimed is:

1. A station for processing analytical samples in individual cuvettes in a device for chemical and biochemical analysis, wherein the station comprises a conveyor for conveying cuvettes to at least one individual processing station, which comprises means for removing individual cuvettes individually from the conveyor, for transferring the cuvettes individually to a position at which a reagent and an individual sample to be analyzed are added and mixed in an individual cuvette, and returning the individual cuvette to the conveyor after adding and mixing the individual sample to be analyzed and the reagent in the individual cuvette.

2. A station according to claim 1, wherein the means for removing individual cuvettes from the conveyor further comprises a change-over and positioning device and a control device, wherein the control device simultaneously controls the motions of i) the change-over and positioning device and ii) a mixing operation during processing of the analytical samples in the individual cuvettes.

3. A pipetting station for pipetting and mixing reagents into samples in individual cuvettes which are to be analyzed, the pipetting station comprising:

a) a pipetting means for pipetting reagents into the individual cuvette when the individual cuvette is in a pipetting and mixing position;

b) a mixing means for mixing the contents of the individual cuvette when the individual cuvette is at the pipetting and mixing position; and c) means for removing the individual cuvette from a cuvette transportation rotor holding the individual cuvette to the pipetting and mixing position, and then returning the individual cuvette to the cuvette transportation rotor after the pipetting of reagents into the individual cuvette, and the mixing of the contents of individual cuvette have occurred.

* * * * *